(12) United States Patent
Le Ouay et al.

(10) Patent No.: US 9,549,878 B2
(45) Date of Patent: Jan. 24, 2017

(54) NANOPARTICLE-CONTAINING IRRIGATION SOLUTION FOR ENDODONTICS

(71) Applicant: MAILLEFER INSTRUMENTS HOLDING Sarl, Ballaigues (CH)

(72) Inventors: Benjamin Le Ouay, Ecublens (CH); Francesco Stellacci, Morges (CH); Janine Conde, Yverdon-les-Bains (CH); Selma Mefti, Lausanne (CH)

(73) Assignee: MAILLEFER INSTRUMENTS HOLDING SARL, Ballaigues (CH)

( * ) Notice: Subject to any disclaimer, the term of this patent is extended or adjusted under 35 U.S.C. 154(b) by 0 days.

(21) Appl. No.: 14/574,515

(22) Filed: Dec. 18, 2014

(65) Prior Publication Data

US 2015/0216765 A1   Aug. 6, 2015

(30) Foreign Application Priority Data

Feb. 6, 2014   (EP) ..................... 14154133

(51) Int. Cl.
| | | |
|---|---|---|
| *A01N 25/00* | (2006.01) | |
| *A61K 6/00* | (2006.01) | |
| *A61L 2/00* | (2006.01) | |
| *A61L 2/238* | (2006.01) | |
| *A61K 8/25* | (2006.01) | |
| *A61Q 11/00* | (2006.01) | |
| *A61K 8/02* | (2006.01) | |
| *A61K 8/19* | (2006.01) | |
| *A61K 8/22* | (2006.01) | |

(52) U.S. Cl.
CPC ........... *A61K 6/0035* (2013.01); *A61K 6/0002* (2013.01); *A61K 8/0241* (2013.01); *A61K 8/19* (2013.01); *A61K 8/22* (2013.01); *A61K 8/25* (2013.01); *A61L 2/0088* (2013.01); *A61L 2/238* (2013.01); *A61Q 11/00* (2013.01); *A61K 2800/413* (2013.01); *A61K 2800/621* (2013.01); *A61K 2800/651* (2013.01); *A61K 2800/882* (2013.01)

(58) Field of Classification Search
None
See application file for complete search history.

(56) References Cited

U.S. PATENT DOCUMENTS

| | | |
|---|---|---|
| 6,924,116 B2 | 8/2005 | Tan et al. |
| 2009/0047222 A1 | 2/2009 | Gu et al. |
| 2011/0262556 A1 | 10/2011 | Holladay et al. |
| 2012/0021034 A1* | 1/2012 | Zink ................ A01N 59/16 424/421 |
| 2013/0115248 A1* | 5/2013 | Lyngstadaas .......... A61K 8/044 424/400 |
| 2014/0308756 A1* | 10/2014 | Gautier ............... B22F 1/0018 436/501 |

FOREIGN PATENT DOCUMENTS

| | | |
|---|---|---|
| AU | 2012100480 A4 | 6/2012 |
| DE | 202008009873 UI | 11/2008 |

OTHER PUBLICATIONS

European Search Report, dated Jun. 25, 2014, from corresponding EP application.

* cited by examiner

*Primary Examiner* — Robert A Wax
*Assistant Examiner* — Quanglong Truong
(74) *Attorney, Agent, or Firm* — Young & Thompson

(57) ABSTRACT

A set of a first and a second preparation are intended to be mixed before or during an endodontic treatment to form an endodontic irrigation solution. The first preparation includes an oxidizing agent. The second preparation includes antibacterial nanoparticles treated to slow their oxidation by the oxidizing agent. The antibacterial nanoparticles are, for example, encapsulated in shells in a hybrid core-shell structure. In one variation, the antibacterial nanoparticles are made from an alloy of at least two elements, one of the elements being more resistant to oxidation than the other.

20 Claims, 3 Drawing Sheets

NANOPARTICLE-CONTAINING IRRIGATION SOLUTION FOR ENDODONTICS

FIELD OF THE INVENTION AND PRIOR ART

The present invention relates to an irrigation solution for endodontics.

During endodontic treatment, the dentist uses an irrigation solution to clean and disinfect the root canal after each filing operation. In fact, the phase of instrumentation of the root canal using mechanised or non-mechanised files creates a large amount of debris which, along with the organic tissue, make up the dentinal sludge. This fine layer which obstructs the dentinal tubules must be removed before the final step of closing the canal. The current prior art recommends systematic rinsing with sodium hypochlorite (NaOCl) after each filing operation, followed by final cleaning with EDTA (ethylene diamine tetraacetic acid), wherein these two irrigation solutions cannot be used simultaneously because one cancels out the action of the other.

Australian patent application no. AU 2012100480 A4 proposes another irrigation solution comprising ethanol, soda (sodium hydroxide) and antibacterial nanoparticles such as nanoparticles of silver, zinc or gold.

Silver nanoparticles are in fact known in the medical field for their antibacterial properties. The antibacterial effect of the silver nanoparticles seems to arise when they are dissolved and $Ag^+$ ions are released. In general, the oxidant permitting dissolution of the silver nanoparticles is dioxygen dissolved in water.

The irrigation solution proposed in the cited Australian patent application is based on this principle of the release of silver ions. However, it is not clearly evident how the dissolution of the nanoparticles in the solution is achieved. The presence of sodium hydroxide in the formulation and the resulting basic pH favour the formation of silver oxide, which actually inhibits the oxidation of these nanoparticles and thus their dissolution, as shown by the diagram in FIG. 1 attached. This results in the action of the nanoparticles during the endodontic treatment, and probably even thereafter, being of a low level.

SUMMARY OF THE INVENTION

The present invention aims to propose a nanoparticle-containing irrigation solution for endodontics in which the lifespan of the nanoparticles can be adjusted in order, for example:

- to correspond to the duration of an endodontic treatment, i.e. about 30 to 60 minutes, for a strong disinfectant action throughout said treatment, or
- to be longer than the duration of an endodontic treatment so that certain partially oxidised particles can remain in the root canal and produce a strong bactericidal action during the hours, or even days, following the treatment.

To this end, the invention provides a set of a first and a second preparation which are intended to be mixed before or during an endodontic treatment to form an endodontic irrigation solution, the first preparation comprising an oxidising agent, the second preparation comprising antibacterial nanoparticles treated to slow their oxidation by the oxidising agent.

Thus in the present invention it is possible to manipulate the two parameters consisting of the quantity of oxidising agent and the protection conferred by the treatment of the antibacterial nanoparticles in order to adjust the lifespan of the nanoparticles, i.e. their rate of dissolution, in a relatively precise manner. The oxidation of the antibacterial nanoparticles begins after the first and second preparations are mixed, causing progressive release of ions which exert an antibacterial action. The two afore-mentioned parameters can be selected to obtain a strong disinfectant effect throughout the endodontic treatment and/or a longer-term effect.

According to one particular embodiment, the antibacterial nanoparticles are encapsulated in shells and thus form therewith hybrid core-shell structures.

The antibacterial nanoparticles are, for example, made from silver, gold, titanium oxide, copper oxide, zinc oxide or chitosan.

The shells are, for example, made of silica, titanium oxide, zirconium oxide or polymer.

The shells are preferably porous, more preferably mesoporous.

The shells advantageously comprise grafted functional groups on their surface.

The oxidising agent is, for example, a peroxide, a hypochlorite, a halogen, a permanganate, a perchlorate or a periodate.

In one particular embodiment, the oxidising agent is hydrogen peroxide.

The first preparation can further comprise a chelating agent, for example maleic acid, citric acid, ethylene diamine tetraacetic acid, malic acid, gluconic acid, lactic acid, glycolic acid, propanoic acid, acetic acid, malonic acid, oxalic acid, tartaric acid, phosphoric acid, a salt of the acids cited above, or ethylene diamine.

The second preparation can further comprise a surfactant such as a sulfate, a sulfonate, a phosphate, an alkyl carboxylate, an alkyl aryl carboxylate, an alkyl ether carboxylate, a quaternary ammonium, a polysorbate or a di- or tri-block polymer. In particular, the surfactant can be cetyl trimethylammonium nitrate.

The first and second preparations are preferably such that the mixture thereof has an acid pH.

The composition of the first preparation is advantageously selected so that the first preparation exerts a cleaning action on the dentine independently of its oxidising action on the antibacterial nanoparticles.

For the same purpose as stated above, the present invention also proposes a set of a first and a second preparation which are intended to be mixed before or during an endodontic treatment to form an endodontic irrigation solution, the first preparation comprising an oxidising agent, the second preparation comprising antibacterial nanoparticles produced from an alloy of at least two elements, one of the elements being more resistant to oxidation than the other element. The two elements are, for example, gold and silver.

DETAILED DESCRIPTION OF SEVERAL EMBODIMENTS

Figure 2:
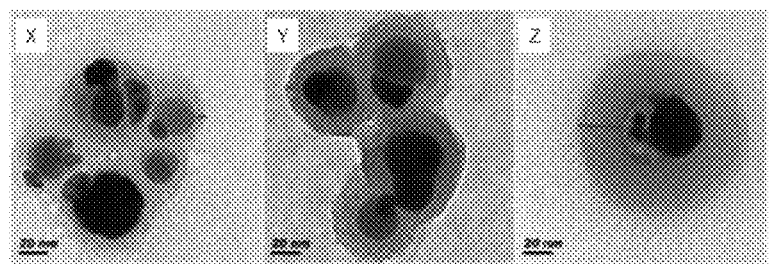
FIG. 2 illustrates silver nanoparticles encapsulated in silica shells of variable thickness (X: 8 nm; Y: 15 nm; Z: 30 nm).

The endodontic irrigation solution in accordance with the invention is obtained by mixing two preparations A and B, preferably being in the form of liquid solutions, preferably aqueous solutions. Solution A contains an oxidising agent and a chelating agent. Solution B contains hybrid nanoparticles with a core-shell structure and a surfactant. "Nanoparticles" are understood within the framework of the present invention to be particles with a diameter of less than 1000 nm, typically between 5 and 1000 nm. In a manner which is known per se, the hybrid nanoparticles with a core-shell structure comprise so-called "core" nanoparticles encapsulated in shells. According to the conditions of synthesis, it is possible that one or more core nanoparticles are encapsulated in a single shell, as shown in FIG. 2. This same FIG. 2 shows that the thickness of the shells is variable. According to the nanoparticle-forming conditions, the shells can be of greater or lesser thickness so as to control the dissolution rate of the core particles, as will be explained hereinunder.

According to a preferred embodiment of the invention, the oxidising agent is hydrogen peroxide (or oxygenated water), the chelating agent is maleic acid, the hybrid nanoparticles comprise silver core nanoparticles and silica shell nanoparticles (Ag@SiO$_2$), and the surfactant is CTAN (cetyl trimethylammonium nitrate).

When the solutions A and B are mixed, the hydrogen peroxide (H$_2$O$_2$) oxidises the metallic silver Ag$^0$ of the nanoparticles to release silver ions Ag$^+$, this species being stable because of the acid pH of the irrigation solution A+B. The silica shell formed around the silver nanoparticles protects these nanoparticles and slows the release of the silver ions which, otherwise, would be released in just some tens of seconds. The combination of an oxidising agent, hydrogen peroxide and of a protective shell around the silver nanoparticles permits the dissolution kinetics of the silver to be regulated so that this dissolution is effected, for example, over a period corresponding to the duration of an endodontic treatment, typically about 30 to 60 minutes, or over a longer period. By means of its chelating action, the maleic acid assists in dissolving the silver nanoparticles once they have been oxidised, by passivating them and preventing the formation of Ag$_2$O. Finally, the CTAN disperses the silver nanoparticles and thus also promotes dissolution thereof.

In addition to their function as mentioned above, the hydrogen peroxide and maleic acid exert a cleaning action on the dentine and a removal action on the dentinal sludge during irrigation of the root canal by the irrigation solution in accordance with the invention. More precisely, the acid and oxidising medium permits the dissolution of inorganic residues (particularly hydroxyapatite) and organic residues (particularly necrotic tissues and bacterial biofilms). Moreover, CTAN renders the silica mesoporous and is also involved in the cleaning of the root canal by its detergent action. The presence of nanoparticles in the irrigation solution also makes it possible to achieve an abrasive action which increases the efficacy of the removal of the dentinal sludge.

Figure 3:
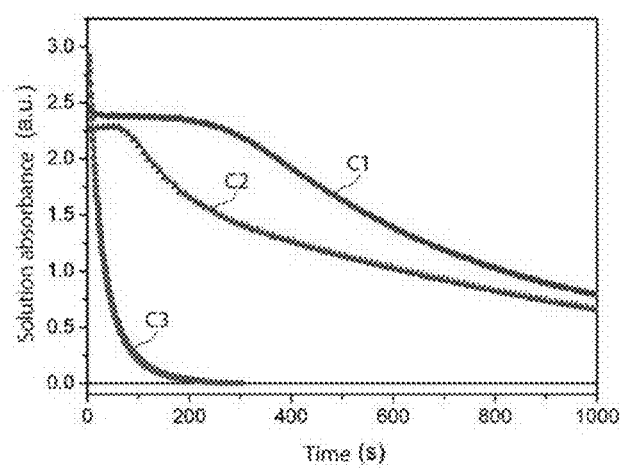
FIG. 3 is a diagram showing the evolution of the absorbance of irrigation solutions as a function of time. In this figure, C1 designates the absorbance curve of an irrigation solution in accordance with the invention containing silver nanoparticles encapsulated in silica shells of a thickness of 30 nm, C2 designates the absorbance curve of an irrigation solution in accordance with the invention containing silver nanoparticles encapsulated in silica shells with a thickness of 15 nm, and C3 designates the absorbance curve of an irrigation solution similar to those of curves C1 and C2 but the silver nanoparticles of which are bare, i.e. not encapsulated in shells.

The endodontic irrigation solution proposed thus exerts two distinct actions:

solution A+B thus permits immediate cleaning on the basis of the oxidising, acid, chelating, detergent and abrasive nature of the various components;

solution A permits the dissolution of the silver nanoparticles to be activated, which contributes to their bactericidal action. The presence of the silica shell around them makes it possible to control the dissolution rate thereof in order to render it compatible with the duration of an endodontic treatment. FIG. 3 shows the progressive reduction in the absorbance of the irrigation solution A+B (cf. curve C1: solution in which the Ag@SiO$_2$ nanoparticles have a SiO$_2$ shell thickness of 30 nm; curve C2: solution in which the Ag@SiO$_2$ nanoparticles have a SiO$_2$ shell thickness of 15 nm) and thus the progressive dissolution of the silver nanoparticles. By way of comparison, FIG. 3 shows that the dissolution of silver nanoparticles without a shell is very rapid and incompatible with the duration of an endodontic treatment (cf. curve C3).

Thus one feature of the present invention resides in the fact that the agents permitting immediate cleaning of the root canal are also those which permit dissolution of the silver nanoparticles.

Figure 1:
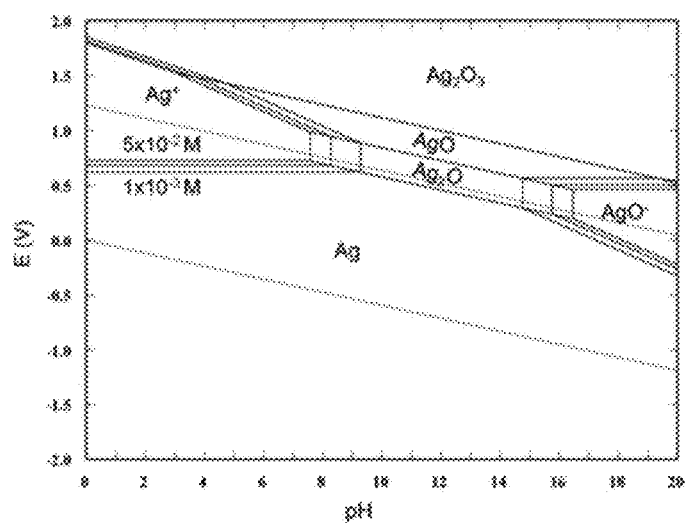
FIG. 1 is a potential-pH diagram (a so-called "Pourbaix" diagram), calculated for silver.
Figure 4:
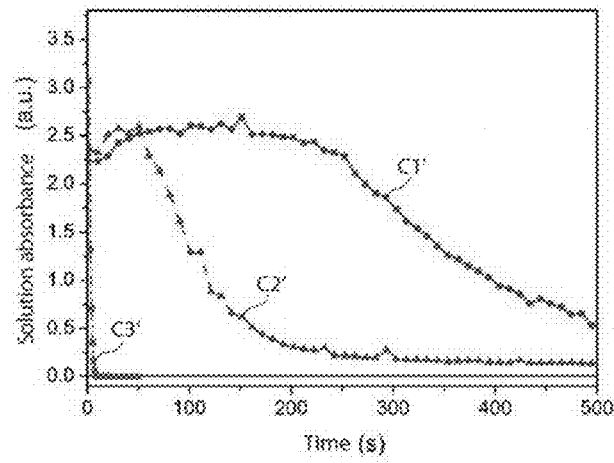
FIG. 4 is a diagram showing the evolution of the absorbance of other irrigation solutions as a function of time. In this figure, C1' designates the absorbance curve of an irrigation solution in accordance with a variation of the invention containing silver nanoparticles encapsulated in silica shells with a thickness of 30 nm, C2' designates the absorbance curve of an irrigation solution in accordance with said variation of the invention containing silver nanoparticles encapsulated in silica shells with a thickness of 15 nm, and C3' designates the absorbance curve of an irrigation solution similar to those of curves C1' and C2' but the silver nanoparticles of which are bare.

In the present invention as described above, progressive dissolution of the silver nanoparticles is possible owing to the fact that an acid-oxidant medium is used where the Ag$^+$ ion is stable in solution (cf. FIG. 1). It is nevertheless possible to consider other means of stabilising the silver ions, for example, by the presence of a high concentration of Cl$^-$ ions or by the presence of ammonia or amines. FIG. 4 shows absorbance curves C1', C2', C3' in such a variation of the invention, where solution A comprises hydrogen peroxide and, instead of maleic acid, ammonium nitrate. The pH of the solution is thus close to 7, and the silver (+1) species are stable in solution owing to the formation of Ag(NH$_3$)$_n^+$ complexes. In this FIG. 4 it can be seen that the point of inflection marking the start of the actual dissolution is located at the same length of time after mixing of solutions A and B (50 s for a shell of 15 nm in thickness, and 250 s for a shell of 30 nm) as in the case of FIG. 3. The dissolution rate is then higher, this mixing being more effective to dissolve the nanoparticles. This testifies to the role of the silica shell around the silver nanoparticles in slowing their dissolution, and this is the case regardless of the solution selected to dissolve them.

In addition to limiting the dissolution rate of the antibacterial nanoparticles, the silica shell can serve as an interface for the grafting of functional groups. In fact, the grafting of groups onto a bare antibacterial nanoparticle, typically of silver, involves fixing the groups directly on the surface atoms of the nanoparticle, for example by means of thiol functions. The presence of such a functionalization may enormously modify the reactivity of the nanoparticles, and thus particularly their dissolution rate. Moreover, as the dissolution of the nanoparticles takes place, the grafted groups would become detached from the surface of the nanoparticle and would thus lose their action. For these reasons, it is preferable to provide around the antibacterial nanoparticle an interface layer on which it is possible to graft the functional groups and which is relatively stable during dissolution of the nanoparticle.

Silica thus constitutes an ideal material to produce this interface layer by reason of its stability in the conditions of the irrigation solution and of the variety of easily available organosilanes, which permits a huge choice of functionalization. Other materials and grafting means can nevertheless be envisaged. Such functionalization is intended to modify the physical or chemical surface properties of the nanoparticles in order to modify their behaviour.

The grafted groups can be:
 small functional groups (sulfonate, ammonium, etc.) serving to modify the surface charge of the nanoparticles and thus their affinity for oppositely charged surfaces, such as the surface of the dentine;
 small functional groups (alkyl, phenyl, alcohol, etc.) serving to modify the hydrophobic/hydrophilic nature of the nanoparticles;
 small functional groups (carboxylates, phosphonates, thiols, amines, etc.) serving to provide the nanoparticles with a greater affinity for one particular type of surface;
 polymeric chains (for example, polyethylene glycol) which can become entangled with the biopolymers and thus preferentially increase adhesion to the bacterial biofilms (mucoadhesion mechanism);
 specific small molecules, able to interact with given molecular receptors, and thus to immobilise the nanoparticles in the proximity of these receptors;
 peptides or proteins which could bind to specific objects (for example, in the membrane of the bacteria) and thus permit precise addressing of antibacterial nanoparticles.

Typically, in solution A, hydrogen peroxide is present at a level of 0.1 to 30% by mass, preferably at a level of about 6%, and the maleic acid is present at a level of 1 to 60% by mass, preferably at a level of about 12%.

In solution B, which can have the same volume as solution A, the quantity of Ag@SiO$_2$ hybrid nanoparticles is typically between 10 and 10000 mg/L, and preferably equal to about 400 mg/L (about 300 mg/L of silver and about 100 mg/L of silica), and the proportion by mass of CTAN is typically between 0.1 and 2.5%, and preferably equal to about 0.5%. The diameter of the silver nanoparticles is typically between 5 and 250 nm, and preferably equal to about 30 nm. The thickness of the silica shells is typically between 2 and 100 nm.

In practice solution A and solution B can be contained in two separate containers, provided to the dentist in the form of a kit. Solution A and solution B can also be contained in two separate compartments of a single container. Solution A is stable over time. Solution B is also stable over time provided it is stored out of contact with oxygen.

Before or during the endodontic treatment, the dentist mixes the two solutions A and B to form the irrigation solution with which he will irrigate the root canal after each instrumentation thereof. The mixing of solutions A and B can also be effected in the tube of the injection system. Mixing the two solutions A and B brings the nanoparticles into contact with the oxidising agent and thus activates the antibacterial effect of the silver, an antibacterial effect which lasts throughout the endodontic treatment owing to the silica shells which slow the dissolution of the silver nanoparticles. In contrast to the silver ions, the silver and silica nanoparticles have a good affinity with the surface of the teeth and easily adhere thereto. At the end of the endodontic treatment the root canal is closed. Some of the partially oxidised silver nanoparticles will be able to remain in the root canal thus closed and continue their disinfecting action for several days after the operation. This will permit a disinfecting action to be achieved, including in the parts of the canal not directly instrumented, by release and diffusion of the silver ions.

Figure 5:
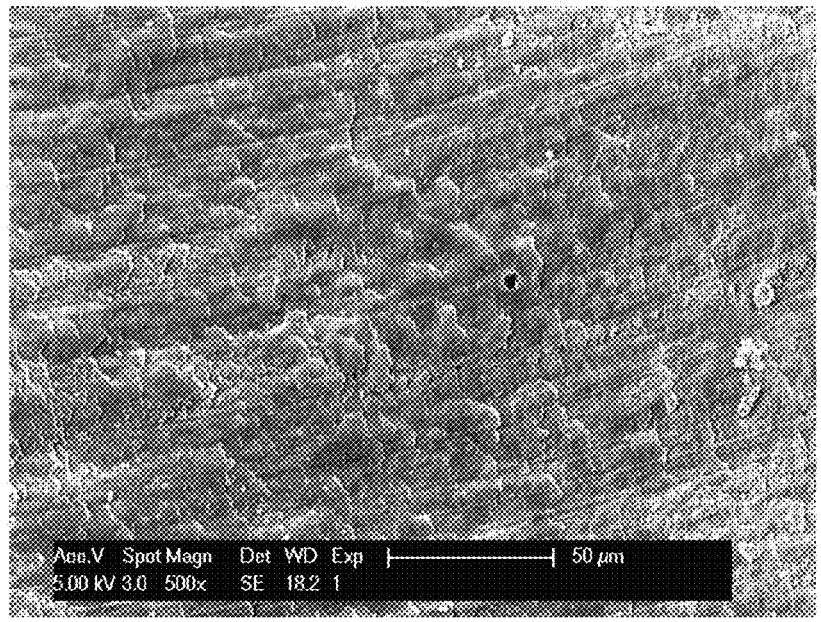
FIG. 5 illustrates dentinal sludge covering the wall of a root canal after instrumentation thereof without irrigation.
Figure 6:
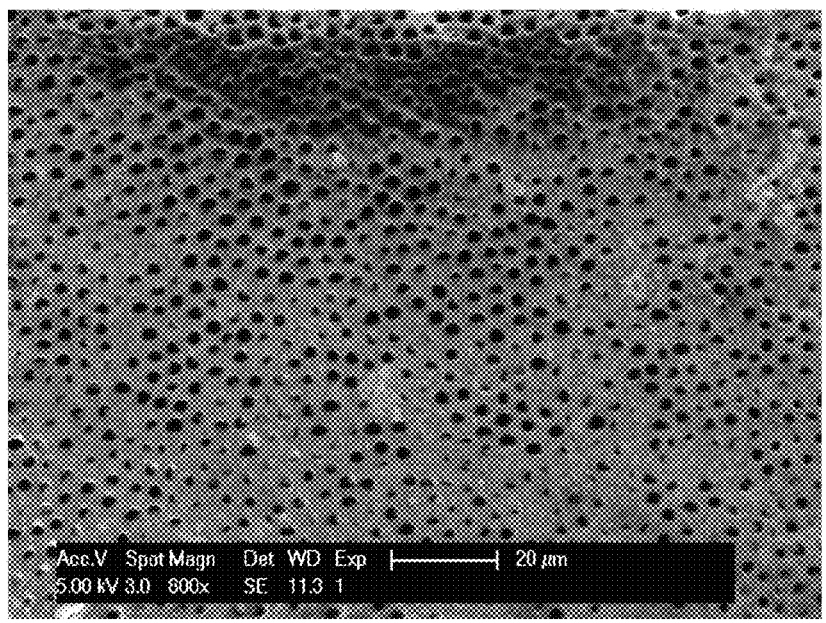
FIG. 6 illustrates the wall of a root canal after instrumentation thereof with irrigation by means of an irrigation solution in accordance with the invention.

By way of illustration, FIG. 5 shows the dentinal sludge which covers the wall of the root canal after instrumentation of said canal without irrigation. FIG. 6 shows the wall of a root canal after instrumentation of said canal with irrigation by means of the solution A+B in accordance with the invention. It will be noted that the dentinal sludge has been removed and that the dentinal tubules are open and non-eroded. The irrigation solution in accordance with the invention, used after each filing operation and also as a final rinsing liquid, permits the surface of the root canals to be cleaned effectively. The silver nanoparticles of solution B can be obtained in a manner which is known per se, for example, from silver nitrate and sodium citrate.

The silica shells can be obtained from APTES (3-aminopropyltriethoxysilane) and TEOS (tetraethylorthosilicate). TEOS forms the largest part of the silica matrix. APTES aids in binding the silica to the surface of the silver (by formation of an Ag—NH$_2$R bond). The thickness of the silica shells can be adjusted, typically between 2 and 100 nm, by adjusting the quantity of TEOS and APTES. It is possible to have a plurality of silica shells sizes (by preparing a number of batches and mixing them) so as to control and to "flatten" the dissolution kinetics. Thus a part of the silver nanoparticles, covered with a thinner silica layer, will have a shorter-term disinfecting effect and another part of the silver nanoparticles, covered with a thicker silica layer, will have a longer-term effect.

Other additives can be used to synthesise the Ag@SiO$_2$ hybrid particles. For example, glycerol makes it possible to obtain a better mono-dispersity of the silver core particles.

In variations of the invention, other oxidising agents could be used as a replacement for, or in addition to, the hydrogen peroxide, for example, another peroxide, a hypochlorite, a di-halogen, a permanganate, a percholate and/or a periodate. Similarly, other chelating agents could be used as a replacement for, or in addition to, maleic acid, for example, citric acid, ethylene diamine tetraacetic acid, malic acid, gluconic acid, lactic acid, glycolic acid, propanoic acid, acetic acid, malonic acid, oxalic acid, tartaric acid, phosphoric acid, a salt of the acids cited above, or ethylene diamine. Halide ions (I$^-$, Br$^-$, F$^-$) can also be used for incorporation into the oxide layer and for promotion of the dissolution of the silver nanoparticles. Finally, CTAB (cetyl trimethylammonium bromide) could replace or be added to the CTAN. However, CTAN is preferred over CTAB because the bromide ion could form an AgBr precipitate which is highly insoluble in the presence of silver, which would reduce the availability thereof. In general, the surfactant can be anionic (such as a sulfate, a sulfonate, a phosphate, an alkyl, alkyl aryl or alkyl ether carboxylate), cationic (such as a quaternary ammonium), zwitterionic or non-ionic (such as a polysorbate or a di- or tri-block polymer).

As explained above, the silver nanoparticles are encapsulated in silica nanoparticles in a core-shell structure to slow their oxidation by the oxidising agent. The shell material could be a material other than silica, for example, titanium oxide, zirconium oxide or a polymer coating. The antibacterial core material could be a material other than silver, for example, gold, titanium oxide, copper oxide, zinc oxide or chitosan.

The oxidation of the antibacterial nanoparticles can also be slowed by treating them in another way than by encapsulating them within a shell. For example, it would be feasible to passivate the surface of the antibacterial nanoparticles by formation thereon of a compound with poor solubility, for example AgBr or $Ag_2S$. In a variation, it would be possible to produce the antibacterial nanoparticles in an alloy which is more resistant to oxidation owing to the greater resistance of one of its elements, for example a gold/silver alloy.

Finally, instead of being in the form of a liquid solution, at least one of preparations A and B could be solid, for example, in the form of a powder. If both preparations A and B are solid, it is possible to envisage the dentist dissolving them himself in water or another liquid.

The invention claimed is:

1. A method, comprising:
    mixing a first and a second preparation to form an endodontic irrigation solution, the first preparation comprising an oxidising agent, the second preparation comprising antibacterial nanoparticles treated to slow their oxidation by the oxidising agent; and
    irrigating with said endodontic irrigation solution in an endodontic treatment.

2. The method as claimed in claim 1, wherein the antibacterial nanoparticles are made from silver, gold, titanium oxide, copper oxide, zinc oxide or chitosan.

3. The method as claimed in claim 1, wherein the antibacterial nanoparticles are encapsulated in shells.

4. The method as claimed in claim 3, wherein the shells are made of silica, titanium oxide, zirconium oxide or polymer.

5. The method as claimed in claim 3, wherein the shells are porous, preferably mesoporous.

6. The method as claimed in claim 3, wherein the shells comprise grafted functional groups on their surface.

7. A method, comprising:
    mixing a first and a second preparation to form an endodontic irrigation solution, the first preparation comprising an oxidising agent, the second preparation comprising antibacterial nanoparticles made from an alloy of at least two elements, one of the elements being more resistant to oxidation than the other element; and
    irrigating with said endodontic irrigation solution in an endodontic treatment.

8. The method as claimed in claim 7, wherein the two elements are silver and gold.

9. The method as claimed in claim 1, wherein the oxidising agent is a peroxide, a hypochlorite, a halogen, a permanganate, a perchlorate or a periodate.

10. The method as claimed in claim 9, wherein the oxidising agent is hydrogen peroxide.

11. The method as claimed in claim 1, wherein the first preparation further comprises a chelating agent.

12. The method as claimed in claim 11, wherein the chelating agent is maleic acid, citric acid, ethylene diamine tetraacetic acid, malic acid, gluconic acid, lactic acid, glycolic acid, propanoic acid, acetic acid, malonic acid, oxalic acid, tartaric acid, phosphoric acid, a salt of the acids cited above, or ethylene diamine.

13. The method as claimed in claim 1, wherein the second preparation further comprises a surfactant.

14. The method as claimed in claim 13, wherein the surfactant is a sulfate, a sulfonate, a phosphate, an alkyl, alkyl aryl or alkyl ether carboxylate, a quaternary ammonium, a polysorbate or a di- or tri-block polymer.

15. The method as claimed in claim 13, wherein the surfactant is cetyl trimethylammonium nitrate.

16. The method as claimed in claim 1, wherein the first and second preparations are such that the mixture thereof has an acid pH.

17. The method as claimed in claim 1, wherein the composition of the first preparation is selected so that the first preparation exerts a cleaning action on the dentine independently of its oxidising action on the antibacterial nanoparticles.

18. An endodontic set, comprising:
    a first and a second preparation adapted to be mixed before or during an endodontic treatment to form an endodontic irrigation solution, the first preparation comprising an oxidising agent, the second preparation comprising antibacterial nanoparticles treated to slow their oxidation by the oxidising agent.

19. An endodontic set, comprising:
    a first and a second preparation adapted to be mixed before or during an endodontic treatment to form an endodontic irrigation solution, the first preparation comprising an oxidising agent, the second preparation comprising antibacterial nanoparticles made from an alloy of at least two elements, one of the elements being more resistant to oxidation than the other element.

20. The method as claimed in claim 1, wherein the antibacterial nanoparticles are encapsulated in shells.

* * * * *

UNITED STATES PATENT AND TRADEMARK OFFICE
CERTIFICATE OF CORRECTION

PATENT NO. : 9,549,878 B2
APPLICATION NO. : 14/574515
DATED : January 24, 2017
INVENTOR(S) : Benjamin Le Ouay et al.

It is certified that error appears in the above-identified patent and that said Letters Patent is hereby corrected as shown below:

In the Claims

Column 8 (Line 50) Claim 20, Line 1:

"20. The method as claimed in claim 1, wherein the"

should be replaced with

--20. The method as claimed in claim 2, wherein the--.

Signed and Sealed this
Twenty-fifth Day of April, 2017

Michelle K. Lee
*Director of the United States Patent and Trademark Office*